(12) United States Patent
Bjerregaard

(10) Patent No.: US 8,192,413 B2
(45) Date of Patent: *Jun. 5, 2012

(54) EXTERNAL URINARY CATHETER

(75) Inventor: Henrik Bork Bjerregaard, Broenshoej (DK)

(73) Assignee: Coloplast A/S, Humlebaek (DK)

( * ) Notice: Subject to any disclaimer, the term of this patent is extended or adjusted under 35 U.S.C. 154(b) by 855 days.

This patent is subject to a terminal disclaimer.

(21) Appl. No.: 11/661,285

(22) PCT Filed: Aug. 29, 2005

(86) PCT No.: PCT/EP2005/054241
§ 371 (c)(1),
(2), (4) Date: Apr. 4, 2008

(87) PCT Pub. No.: WO2006/021590
PCT Pub. Date: Mar. 2, 2006

(65) Prior Publication Data
US 2008/0195067 A1 Aug. 14, 2008

(30) Foreign Application Priority Data
Aug. 27, 2004 (EP) ................................... 04020368

(51) Int. Cl.
*A61F 5/44* (2006.01)
(52) U.S. Cl. ........................ 604/352; 604/355
(58) Field of Classification Search .................. 604/346, 604/347, 349–352, 355; 128/842, 844
See application file for complete search history.

(56) References Cited

U.S. PATENT DOCUMENTS

| | | | |
|---|---|---|---|
| 3,648,700 A | | 3/1972 | Warner |
| 4,378,018 A | * | 3/1983 | Alexander et al. ............ 604/350 |
| 4,388,923 A | * | 6/1983 | Heimreid ..................... 604/352 |
| 4,586,974 A | * | 5/1986 | Nystrom et al. ............... 156/165 |
| 4,769,099 A | | 9/1988 | Therriault et al. |
| 4,865,595 A | * | 9/1989 | Heyden ......................... 604/352 |
| 4,885,049 A | | 12/1989 | Johannesson |
| 4,932,948 A | | 6/1990 | Kernes et al. |
| 5,423,784 A | * | 6/1995 | Metz ............................. 604/351 |
| 5,554,141 A | * | 9/1996 | Wendler ........................ 604/352 |
| 5,685,870 A | * | 11/1997 | Tanghøj ........................ 604/349 |
| 5,779,964 A | | 7/1998 | Welch et al. |
| 5,836,307 A | * | 11/1998 | Scholl ........................... 128/844 |
| 5,942,186 A | * | 8/1999 | Sanada et al. .................. 422/57 |
| 2004/0006321 A1 | | 1/2004 | Cheng |
| 2008/0249489 A1 | * | 10/2008 | Rasmussen et al. .......... 604/352 |

FOREIGN PATENT DOCUMENTS

| | | |
|---|---|---|
| DE | 4130220 | 12/1992 |
| EP | 0 508 584 A1 | 10/1992 |
| JP | 2002-325786 | 12/2002 |

\* cited by examiner

*Primary Examiner* — Tatyana Zalukaeva
*Assistant Examiner* — Benedict L Hanrahan
(74) *Attorney, Agent, or Firm* — Coloplast Corp., Coloplast A/S; Daniel G. Chapik; Nicholas R. Baumann

(57) ABSTRACT

The external urinary catheter comprises a sheath portion (1) and a tip portion (3). A layer of adhesive (7) is provided on the inner side of the sheath portion (1) and extends between a first limit (7*a*) and a second limit (7*b*). At least one indication (8) indicating at least the first limit (7*a*) of the layer of adhesive (7) is provided. The indication may be a visual indication, e.g. in the form of a colored line (8).

8 Claims, 1 Drawing Sheet

EXTERNAL URINARY CATHETER

This is a national state of PCT/EP05/054241 filed Aug. 29, 2005 and published in English.

The present invention relates to an external urinary catheter comprising a sheath portion and a tip portion, said sheath portion extending between said tip portion and an open end, a layer of adhesive being provided on an inner side of said sheath portion and extending between a first limit and a second limit.

External urinary catheters, or urisheaths, are conventionally used for aiding male urinary incontinence and for use in hospitals in connection with treatment and surgery of urethral disorders. Such an external urinary catheter normally comprises a sheath or body portion, which in the mounted condition encloses the shaft of the penis, and a tip portion which via a hose is intended to be connected to a urine collection bag that is e.g. fastened to the bed or the leg of the user.

Traditionally, the external urinary catheter is delivered in a rolled-up condition. In this delivery condition, the sheath portion is rolled-up in a number of successive windings to such an extent that the layer of adhesive is entirely accommodated in the windings to allow the urisheath to be packaged and handled without the inner side of the sheath portion adhering to the surroundings. In order to apply the external urinary catheter on a penis, the sheath portion is unrolled slightly until the layer of adhesive on the inner side of the sheath portion is exposed. In this condition, the external urinary catheter is positioned on the penis such that the layer of adhesive is brought into contact with the skin and the remaining part of the sheath portion is subsequently unrolled.

When applying the external urinary catheter it is essential that it be positioned correctly before the adhesive contacts the skin. The initial tack of the adhesive is relatively high and it may be difficult to refit an external catheter that has been positioned incorrectly. In some cases the external urinary catheter even has to be replaced by a new one after an unsuccessful attempt has been made.

These difficulties are particularly pronounced in the case of disabled users, who most often require help to be able to perform the mounting of the urinary catheter. Such help is costly and since most users consider mounting of urinary catheters to be a private matter, they consider it more or less unpleasant.

With this background it is the object of the present invention to provide an external urinary catheter of the kind mentioned in the introduction, which overcomes or at least alleviates the above-mentioned disadvantages.

This and further objects are met by the provision of an external urinary catheter comprising a sheath portion and a tip portion, said sheath portion extending between said tip portion and an open end, a layer of adhesive being provided on an inner side of said sheath portion and extending between a first limit and a second limit, that the sheath portion is adapted to be rolled-up in a number of successive windings, said external urinary catheter being characterized in that the external urinary catheter comprises at least one indication indicating at least the first limit of the layer of adhesive.

The invention is based on the recognition that it may be difficult to detect when the adhesive starts to contact the skin, especially when the sheath portion is rolled up. By adding an indication, the beginning of the layer of adhesive, i.e. the first limit, is detectable. This in turn will help the person fitting the external urinary catheter. The sheath portion can safely be unrolled to a point just before the adhesive contacts the skin. With the external urinary catheter positioned correctly, the sheath portion can then be unrolled further for the adhesive to contact the skin.

It should be understood that implicit indication means, such as for example release liners can not be used when the sheath portion is rolled up, since the release liner would wrinkle together and be displaced. Furthermore, such release liners are typically unnecessary since the material of newer urisheath in itself works as release liner, such as for example urisheaths made of silicone. Therefore is it necessary to provide alternative indications for urisheaths where the sheath portion is rolled up.

Furthermore is it often necessary for additional indications since the sheath portion is rolled up and therefore is the adhesive limit often difficult to detect, especially when the sheath portion is transparent, or at least partly transparent, as the overlapping layers will create a diffused view of the adhesive layer.

Thus, it is possible even for disabled users to handle mounting of the external urinary catheter according to the invention without the need for assistance from a medical staff. As a consequence, users experience a more comfortable mounting of the urinary catheter, and medical personnel may be saved.

In an embodiment of the invention, the indication is a visual indication.

The visibility may be provided by means of a colour. This makes the first limit of the layer of adhesive immediately recognizable, and the colour may be easily applied during the production of the external urinary catheter, thus entailing only low or no additional production costs. In one embodiment, the indication is in the form of a coloured line. As an alternative, the indication is provided by a colouring of the layer of adhesive.

The choice of the at least one indication as a colour has a further advantage, namely that if different size external urinary catheters have different indication colours, the indication can additionally be used to identify the size of the external urinary catheter.

Alternatively, or additionally, the at least one indication may be a tactile indication. This entails that even users having impaired eyesight may perform the mounting. Preferably, such a tactile indication comprises a plurality of circumferential protrusions along said first limit.

In the following the invention will be described in further detail with reference to the schematic drawings, in which FIG. 1 shows a side view of a first embodiment of the external urinary catheter according to the invention in a rolled-up condition;

Figure 1:
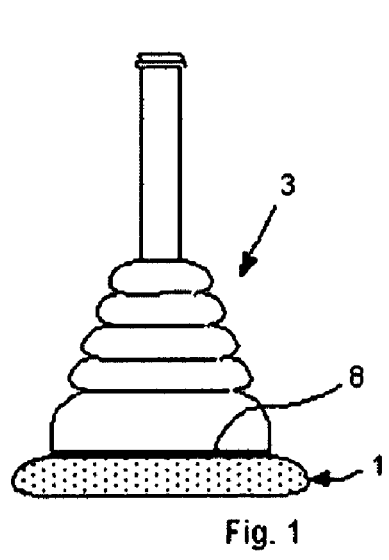
Figure 2:
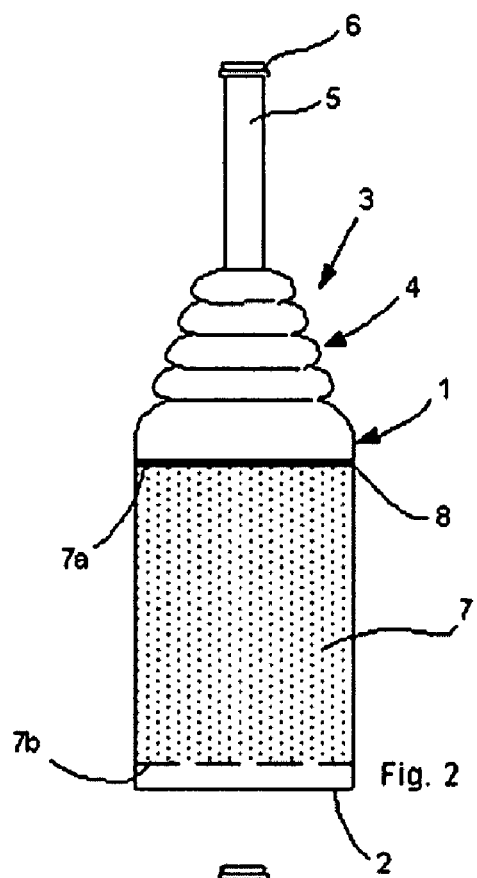
FIG. 2 shows a side view of the urinary catheter of FIG. 1 in an unrolled condition.

The structure of the external urinary catheter according to the invention will be described with reference to the first embodiment of FIGS. 1 and 2. In the second and third embodiments of FIGS. 3 and 4, respectively, elements having the same or analogous function as in the first embodiment are denoted by the same reference numerals, and only differences in relation to the first embodiment will be described in detail.

The external urinary catheter comprises a soft thin-walled and flexible sheath portion 1 with an open end 2. At the end opposite the open end 2 the sheath portion 1 is connected to or formed integrally with a tip or end portion 3. The sheath portion 1 is intended for mounting on the penis of a user (not shown), and the tip portion 3 is intended for connecting the urinary catheter to a urinary bag or the like (not shown) by means of a hose (not shown either).

The sheath portion 1 is made from any suitable material. Advantageously, the sheath portion is to some extent transparent, the term "transparent" being intended to be understood in such a way that it is possible to inspect at least some areas of the penis without removing the external urinary catheter.

The tip portion 3 comprises an anti-kinking chamber provided by a flexible bellows portion 4, and a tip connector 5. The four annular parts of the bellows portion 4 may be arbitrarily compressed, whereby the tip connector 5 may be directed at any angle to the longitudinal axis of the external urinary catheter less than approximately 90°. This prevents blockage of the hose leading to the urinary bag and allows for movement of the catheter independently from the urinary bag. In the embodiment shown, the tip connector 5 is furthermore provided with a circumferential bead 6.

In order to secure the external urinary catheter to the penis of the user, part of the inner side of the sheath portion 1 is provided with a layer of a suitable adhesive. The adhesive layer, which is denoted by 7 in the embodiment of FIGS. 1 and 2, may e.g. be provided as a layer or a coating of a pressure-sensitive adhesive having a relatively high permeability to water vapour. The layer of adhesive extends between a first limit 7a in the vicinity of the tip portion 3 and a second limit 7b, which in the embodiment shown is situated near the open end 2. However, other extensions of the layer of adhesive 7 are of course conceivable. In the first embodiment, the adhesive layer 7 is virtually transparent and the shading shown in FIG. 2 is for reasons of readability only, as is the broken line indicating the second limit 7b.

Eventually, the external urinary catheter is provided with an indication, the function of which will be described in detail further down. In the embodiment of FIGS. 1 and 2, the indication is in the form of a coloured line 8. The coloured line 8 is positioned at the beginning of the layer of adhesive 7 such that it substantially coincides with the first limit 7a. It is also possible to position the coloured line 8 slightly offset with respect to the first limit 7a.

The urinary catheter is delivered to the user in a rolled-up condition. In this condition the sheath portion 1 is rolled upon itself in successive windings, starting from the open end 2 towards the tip portion 3. In order to prevent successive windings in the rolled-up sheath portion 1 from sticking together, the outer side is provided with adhesive-rejecting properties in a manner known per se. In this rolled-up delivery condition, the layer of adhesive 7 is not exposed, i.e. the coloured line 8 and the first limit 7a are positioned within the windings.

When the external urinary catheter is to be mounted on a user, the sheath portion 1 is unrolled slightly until the indication in the form of the coloured line 8 appears and is visible to the person performing the mounting, either from the outer side or the inner side of the external urinary catheter. This slightly unrolled condition corresponds in substance to the condition shown in FIG. 1, depending on the exact position of the coloured line 8 with respect to the first limit 7a. At this point, the external urinary catheter is positioned on the penis of the user. Further unrolling of the sheath portion 1 entails that the external urinary catheter is held in position by the adhesion provided by the contact between the layer of adhesive 7 and the skin. Subsequently, the remaining part of the sheath portion 1 is unrolled until the sheath portion 1 surrounds the shaft of the penis at least partly.

Figure 3:
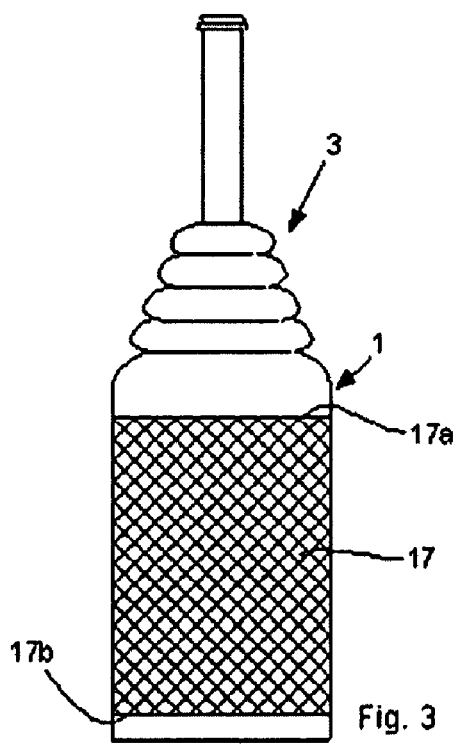
FIG. 3 shows a side view corresponding to FIG. 2 of a second embodiment of the external urinary catheter according to the invention.

Referring now to FIG. 3, the layer of adhesive 27 in the second embodiment extends between first and second limits 27a and 27b, corresponding to the first embodiment. However, the indication marking the beginning of the layer of adhesive 27, i.e. at least the first limit 27a, is provided by a colouring of the layer of adhesive 27 itself. This colouring may be accomplished in any suitable manner, e.g. by utilizing an adhesive that is inherently coloured or a separate colouring agent or pigment may be added.

Figure 4:
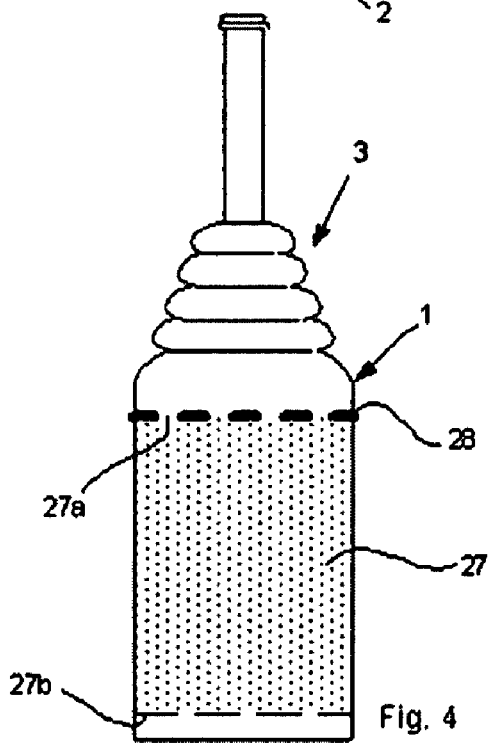
FIG. 4 shows a side view corresponding to FIG. 2 of a third embodiment of the external urinary catheter according to the invention.

In the third embodiment shown in FIG. 4 the indication marking the beginning of the layer of adhesive 27 extending between first and second limits 27a and 27b is a tactile indication. The indication comprises a plurality of circumferential protrusions 28 along the first limit 27a.

It is of course possible to combine different indications in one external urinary catheter, e.g. an indication that is mainly tactile may also to some extent be visible and vice versa. Indications having an audible element are also conceivable, e.g. a cracking sound that is activated when the beginning of the layer of adhesive on the sheath portion is exposed. It is also possible to have more than one indication.

The invention should not be regarded as being limited to the embodiments described in the above but various combinations and modifications may be carried out without departing from the scope of the following claims.

For example, although the invention has been described only with respect to external urinary catheters for positioning on the penis, it is of course possible to apply it to other products, in which adhesive contact between the product and the skin is involved. Evidently, the invention may as well be applied to surgical gloves, contraceptive condoms, fingerstalls etc.

The invention claimed is:

1. An external urinary catheter comprising:
   a sheath portion and a tip portion, said sheath portion extending from said tip portion to an open end, a layer of adhesive provided on an inner side of said sheath portion between a first limit adjacent said tip portion and a second limit adjacent said open end, wherein said sheath portion is rolled in successive windings from said open end toward said tip portion such that the layer of adhesive is covered by and located within said successive windings of said sheath portion and said external urinary catheter includes an coloured line indicating a location of said first limit that is a different colour from the remaining sheath portion.

2. An external urinary catheter according to claim 1, in which said indication is a visual indication.

3. An external urinary catheter according to claim 2, in which said indication is provided by a colouring of the layer of adhesive.

4. An external urinary catheter according to claim 1, in which said indication is a tactile indication.

5. An external urinary catheter according to claim 4, in which said at least one indication comprises a plurality of circumferential protrusions along said first limit.

6. An external urinary catheter according to claim 1 comprising a plurality of indications indicating a location of said first limit.

7. An external urinary catheter according to claim 1, wherein said indication indicates through said sheath portion a visual location of said first limit of the layer of adhesive.

8. An external urinary catheter comprising:
   a catheter delivered to a user in a rolled-up delivery condition, the catheter including a sheath portion and a tip portion, said sheath portion extending between said tip portion and an open end with a layer of adhesive provided on an inner side of said sheath portion between a first limit and a second limit where said first limit is nearer to said tip portion than said second limit is to said tip portion;

wherein said sheath portion is rolled in successive windings from said open end toward said tip portion such that the layer of adhesive is interior said successive windings of said sheath portion and said external urinary catheter including an indicator of a location of said first limit of said layer of adhesive;

wherein said indicator is a coloured line that is a different colour from the remaining sheath portion.

* * * * *